United States Patent [19]

Takano et al.

[11] 4,246,430

[45] Jan. 20, 1981

[54] METHOD FOR PRODUCING CRYSTALS OF SORBIC ACID

[75] Inventors: Masaaki Takano; Masahiro Nakashima, both of Minamatashi, Japan

[73] Assignee: Chisso Corporation, Osaka, Japan

[21] Appl. No.: 967,143

[22] Filed: Dec. 6, 1978

[30] Foreign Application Priority Data

Dec. 22, 1977 [JP] Japan ............................ 52/154827

[51] Int. Cl.³ ..................... C07C 51/43; C07C 57/10
[52] U.S. Cl. ................................................ 562/600
[58] Field of Search ........................... 562/600, 601

[56] References Cited

U.S. PATENT DOCUMENTS

| | | | |
|---|---|---|---|
| 3,056,830 | 10/1962 | Koopal et al. | 562/601 |
| 3,574,728 | 4/1971 | Takasu et al. | 562/601 |
| 3,997,598 | 12/1976 | Fernholz et al. | 562/600 |

FOREIGN PATENT DOCUMENTS 42-23168  11/1967  Japan ................................ 562/601

*Primary Examiner*—Vivian Garner
*Attorney, Agent, or Firm*—Fred Philpitt

[57] ABSTRACT

A method for producing crystals of sorbic acid by recrystallization with an aqueous solution of an alcohol and wherein an alkali metal ion is employed as a crystal-modifying ion.

According to this method, a recrystallized product of sorbic acid having a superior hardness, bulk density, fluidity, etc. is obtained.

4 Claims, No Drawings

METHOD FOR PRODUCING CRYSTALS OF SORBIC ACID

DESCRIPTION OF THE INVENTION

This invention relates to a method for producing crystals of sorbic acid. More particularly, it relates to a method for producing crystals of sorbic acid having good qualities by using a crystal-modifying ion.

The purification of crystals of sorbic acid having good qualities as a food-preserving agent has been carried out mainly by recrystallization processes. As a recrystallization solvent, water or an organic solvent has been used. The properties which may become a problem as a result of these recrystallization processes are particle size, distribution of particle size, hardness, color, fluidity, stability, etc. Among these processes, for the improvement of stability, there is known a method disclosed in the official gazette of Japanese patent publication No. 2449 of 1969, etc. However, no concrete methods have been disclosed for maintaining particle size distribution, hardness, fluidity, etc. in the range of numerical values which are preferable for the use of sorbic acid products.

Further, it has been known that the addition of a metal cation, as a crystal-modifying ion generally brings about various desirable results, in the case of crystallization of a specified compound (for example an inorganic salt) from an aqueous solution (Crystallization, No. 3 of design and operation series, pages 21–27, by Aoyama and Toyokura, issued by Kagaku Kogyo-sha). However, nothing has been known about the crystal-modifying effect of a metal cation at the time of crystallization of an unstable organic acid such as sorbic acid from an aqueous solution of alcohol.

Said term "crystal-modifying" has been this time translated from Japanese term "Baisho".

"Baisho" effect is defined as an effect brought by adding a small amount of a substance to a solution to be subjected to crystallization, at the time of crystallization to modify the properties of the crystals. Due to the addition, for example, not only the crystallization rate but also the nucleation, crystal habit, crystalline phase, etc. are varied, and hence the shape, size, transparency and further, important intrinsic physical properties, etc. of crystals are varied.

We have made comprehensive studies on the effects of crystal-modifying agents at the time of crystallization of sorbic acid by way of recrystallization from water or an organic solvent, and quite unexpectedly found a method which provides products having excellent particle size distribution, hardness, fluidity and bulk density and which does not require strict control for the conditions of crystallization, by the simultaneous use of a specified solvent mixture of water-alcohol and an alkali metal ion.

As is evident from the foregoing description, a first object of the present invention is to provide a novel method for producing sorbic acid crystals in which a crystal-modifying agent is used. A second object of the present invention is to provide a method for producing sorbic acid crystals having excellent particle size distribution, hardness, fluidity and bulk density. A third object of the present invention is to provide sorbic acid crystals having various excellent properties such as above-mentioned. Other objects and advantages will be apparent from the description which hereinafter follows.

The present invention resides in:

(1) A method for producing sorbic acid crystals which is characterized in the use of an alkali metal ion as a crystal-modifying ion in the production method of sorbic acid crystals carried out by recrystallization with an aqueous solution of alcohol as a solvent;

(2) a method as described above in (1) in which the alcohol used is a monovalent lower aliphatic alcohol;

(3) a method as described above in (1) and (2) in which the alkali metal ion used is sodium ion or potassium ion;

(4) a method as described above in (1) to (3) in which a compound as a source from which the alkali metal ion is produced is a salt of an inorganic acid such as an alkali metal hydroxide, halide, carbonate, sulfate, borate, phosphate, phosphite or the like, and an alkali metal salt of an aliphatic monocarboxylic acid, aliphatic polycarboxylic acid, aromatic carboxylic acid or aliphatic oxycarboxylic acid; and (5) a method as described above in (1) to (4) in which the temperature of the aqueous solution of alcohol at the time of dissolving sorbic acid therein is in the range of 20° C. to 70° C.

More detailed explanation will be given with regard to the concrete contents of the present invention.

(i) As for the sorbic acid employed in the method of the present invention, it is possible to employ a raw sorbic acid, as it is, which is obtained according to a known method, for example, by acid-decomposition or heat-decomposition of a polyester obtained by condensing ketene with crotonic aldehyde, but it is preferable to employ a sorbic acid having been subjected to a preliminary purification step e.g. by decoloration with active carbon, since the method of the present invention does not provide any specific effect as compared with those of conventional recrystallization process, upon decoloration, removal of impurities, etc. of raw sorbic acid.

(ii) The details of the aqueous solution of alcohol employed in the method of the present invention are as follows:

As for water, it is desirable to employ deionized water or distilled water, but it is also possible to employ softened water so long as it does not cause any obstacle, considering the amount of the alkali metal ion used in the method of the present invention as mentioned below. Further as for the alcohol, lower aliphatic saturated monovalent alcohols described above in the item (2) may be employed, and among these, methanol, ethanol and isopropanol which are optionally miscible with water are most preferable. However, it is also possible to employ monovalent alcohols such as butanol, isobutanol, etc. so long as they are optionally miscible with water when simultaneously employed with the above-mentioned alcohols. Although higher aliphatic saturated monovalent alcohols other than the foregoing can be also employed, there is a tendency that they are liable to remain in a larger amount in the product of sorbic acid after crystallization, washing and drying, depending upon the amount to be admixed. Thus, in case where said washing and drying are carried out smoothly, it is possible to simultaneously employ even aliphatic monovalent alcohols having 5 carbon atoms or more.

In addition, it is also possible to employ other water-soluble organic solvents such as ketones, e.g., acetone, cyclic ethers, e.g. dioxane, etc. at the same time with the lower aliphatic saturated monovalent alcohols described above in the item (2), to such an extent that the effectivenesses of the present invention are not injured.

However, polyhydric alcohols such as ethylene glycol, propylene glycol, glycerol, etc. cannot be substituted for the alcohols described in the item (2).

The proportion of alcohols to water employed is 20–90% by weight, preferably 30–80% by weight. If the proportion is less than 20% by weight or more than 90% by weight, recrystallization itself is possible, but the effectivenesses of the simultaneous use of the crystal-modifying additive as mentioned below are much reduced, or cannot be exhibited. The mixing manner of the alcohol with water has no particular limitation.

(iii) The crystal-modifying additive ion employed in the method of the present invention is an alkali metal ion, and sodium ion and potassium ion are preferable since they are easily used. Its effective concentration range is 0.0001 mol to 1 mol, preferably 0.001 mol to 0.1 mol, based on 1000 g of the above-mentioned aqueous solution of alcohol. If the concentration of the crystal-modifying additive ion is lower than the above-mentioned range, the effectivenesses cannot be exhibited or are insufficient; while if it is higher than the above-mentioned range, the dissolution of sorbic acid in the aqueous solution of alcohol is restricted, or the amount thereof attached to the crystallized product increases, and on the other hand, the aimed improvement in the physical properties such as particles size distribution, etc. cannot be attained. As for the compound as a source from which the crystal-modifying ion is produced (which will often be hereinafter referred to as crystal-modifying agent), there can be employed for example, usual alkali metal hydroxides such as sodium hydroxide, potassium hydroxide, or alkali metal salts such as halides, e.g., sodium chloride, potassium chloride, sodium bromide, carbonates, e.g., sodium carbonate, sulfates, e.g., sodium sulfate, borates, e.g., sodium borate, sodium phosphate ($Na_3PO_4$), organic acid salts of alkali metals such as alkali metal salts of aliphatic monocarboxylic acids, e.g., acetic acid, propionic acid, butyric acid, isobutyric acid, crotonic acid, caproic acid, sorbic acid and octylic acid, aliphatic dicarboxylic acids, e.g., malonic acid, succinic acid, fumaric acid, maleic acid and adipic acid, aliphatic oxypolycarboxylic acids, e.g., malic acid, tartaric acid and citric acid, etc.

Further it is also possible to employ alkali metal salts of glycolic acid, lactic acid, benzoic acid, l-ascorbic acid, l-glutamic acid and erysorbic acid, as well.

Even in the case of inorganic or organic acid salts other than the foregoing, compounds which form crystal-modifying ion when they are dissolved in the aqueous solution of alcohol are effective in the present invention, in crystallization but salts having a poisonous property (e.g. NaCN) are undesirable so long as the sorbic acid is to be used as a food additive and also those having a dangerous property at the time of handling, such as explosiveness.

Further, even in case of phosphoric acid salts, polymeric phosphoric acid salts such as sodium triphosphate have no effectiveness, and also, even in case of organic acid salts, high molecular weight organic acid salts such as sodium polyacrylate, when singly used as an alkali metal ion-generating agent, hinder the growth of crystals, whereas, when used in combination with another crystal-modifying agent as described above in the item (4), such an inhibition effect not only disappears, but also particular effectiveness such as slendering or slight flattening of the shape of the resulting crystal of sorbic acid is exhibited.

(iv) Crystallization conditions:

The concentration of sorbic acid, the dissolution temperature and stirring condition for the crystallization and others are as follows:

Ⓐ The concentration of sorbic acid has no particular limitation, but 10 to 100 parts by weight of sorbic acid based on 100 parts by weight of the aqueous solution of alcohol as solvent are easily operable, taking into account the dissolving ability of the aqueous solution of alcohol employed and the dissolution temperature. If the concentration is lower than 10 parts by weight, the operational efficiency is reduced; while if it exceeds 100 parts by weight, agitation as mentioned below becomes difficult to a certain extent, and the crystallization is liable to become rapid, resulting in a difficult operation.

Ⓑ The dissolution temperature for crystallization has no particular limitation, but 10° C. to 80° C., preferably 20° C. to 70° C. are easily operable, taking into account the boiling point (in case of the atmospheric pressure) of the aqueous solution of alcohol, and the sorbic acid or crystal-modifying agent-dissolving ability thereof and the cooling manner for the crystallization.

Ⓒ The stirring condition of the aqueous solution of alcohol containing sorbic acid has no particular limitation.

Namely, the solution may be allowed to stand, and even when it is stirred slowly or considerably vigorously in the vessel, the resulting crystalline particles do not become notably small. However, powerful stirring to such an extent that the whole of the solution moves to the wall of the vessel due to the centrifugal force caused by the stirring or the solution notably bubbles in the vessel as if it were boiling, is unnecessary and rather hinders the growth of crystals. Thus, stirring may be carried out to such an extent that the solution moves slowly, and even when the stirring condition is somewhat varied, the particle size distribution, etc. of the resulting crystals of sorbic acid will not be notably nor rapidly varied.

(v) Case where no crystal-modifying agent is employed:

In this case, as apparent from Comparative examples mentioned later, it is difficult to adjust the purity of sorbic acid employed, the composition of the aqueous solution of alcohol employed, and the dissolving and cooling conditions; the reproducibilities of particle size distribution, etc. are poor; and the expected hardness and fluidity cannot be exhibited. The effectivenesses of the method of the present invention as revealed in the foregoing description are summarized as follows:

Ⓐ A novel method for recrystallizing sorbic acid wherein a crystal-modifying agent is employed in combination with a specified solvent mixture, has been revealed.

Ⓑ It is possible to produce a product of recrystallized sorbic acid with a good reproducibility.

Ⓒ It is also possible to produce a product of recrystallized sorbic acid having superior hardness, bulk density and fluidity to those obtained according to known methods (wherein either water, water-an organic solvent or an organic solvent is employed).

Ⓓ It does not matter if a stabilizer (e.g. sodium sorbate) is at the same time employed, which results in a product having a good stability.

Ⓔ The amount of fine powder formed is small, and hence even in the case where the fine powder is recovered and reused, the yield of recrystallized product is substantially improved.

Examples are illustrated below, and it goes without saying that the method of the present invention is not intended to be limited thereby.

EXAMPLE 1

Two Kg of a raw sorbic acid obtained by heat-decomposing a polyester obtained by condensing ketene with crotonaldehyde, followed by decoloration with active carbon, 2 g of sodium hydroxide and 6 Kg of an aqueous solution of ethanol having a concentration of 50% by weight, were fed to a 10 l capacity, stainless steel stirring vessel (the inner diameter of the vessel: 240 mm, the width of the stirring blades: 20 mm, and the length thereof: 160 mm), and dissolved together by heating up to 70° C., and thereafter cooled down to 30° C. over 6 hours with stirring at a revolution number of 500 rpm (with which the solution inside the vessel was in a turbulent state and vigorously bubbled with air involved therein), to crystallize sorbic acid.

After separating the mother liquor by filtration, water-washing and drying were carried out in a conventional manner to give crystalline particles of sorbic acid (yield: 1570 g) which had a round shape, a very good fluidity and a hardness to such an extent that even when pressed with the tips of fingers, they were not crushed to pieces.

Further, the particle size distribution was as follows, and the bulk density of a portion having a particle size of 20 mesh pass and 42 mesh on among them was measured to give 0.71 g/ml.

| Particle size distribution | 20 mesh on: | trace % by weight |
|---|---|---|
| | 20 mesh pass, 42 mesh on: | 94% by weight |
| | 42 mesh pass, 60 mesh on: | 4% by weight |
| | 60 mesh pass: | 2% by weight |

COMPARATIVE EXAMPLE 1

Recrystallization was carried out under the same conditions as those of Example 1 except that no sodium hydroxide was added. As a result, the resulting crystals had a small particle size as mentioned below and were soft and readily crushed to such an extent that they were crushed when pressed with the tips of fingers and their fluidity was also inferior (yield: 1550 g).

| Particle size distribution | 20 mesh on: | 0% by weight |
|---|---|---|
| | 20 mesh pass, 42 mesh on: | 1% by weight |
| | 42 mesh pass, 60 mesh on: | 5% by weight |
| | 60 mesh pass: | 94% by weight |

The bulk density of a portion having a particle size of 42 mesh pass and 60 mesh on was measured to give 0.51 g/ml. In addition, the bulk density of a portion having a particle size of 60 mesh pass was 0.46 g/ml.

EXAMPLE 2

1900 Grams of the same sorbic acid as in Example 1, 5 g (0.013 mol) of sodium phosphate and 6000 g of an aqueous solution of methanol having a concentration of 50% by weight were fed to the same stirring vessel as in Example 1, and dissolved together by elevating the temperature up to 68° C., and thereafter cooled down to 30° C. over 5.5 hours with stirring at a revolution number of 450 rpm (the state inside the vessel was almost the same as in Example 1), to effect crystallization.

After separating mother liquor by filtration, water-washing and drying were carried out in a conventional manner. The resulting crystals of sorbic acid (yield: 1460 g) had a round shape and were very good both in the hardness and fluidity.

The particle size distribution was as follows, and the bulk density of a portion having a particle size of 20 mesh pass and 42 mesh on, among them, was measured to give 0.72 g/ml.

| Particle size distribution | 20 mesh on: | 0% by weight |
|---|---|---|
| | 20 mesh pass, 42 mesh on: | 95% by weight |
| | 42 mesh pass, 60 mesh on: | 4% by weight |
| | 60 mesh pass: | 1% by weight |

COMPARATIVE EXAMPLE 2

Recrystallization was carried out under the same conditions as those in Example 2 except that no sodium phosphate was added, to give crystals which were soft and inferior in the fluidity (yield: 1440 g). The particle size distribution was as follows, and the bulk density of a portion having a particle size of 42 mesh pass and 60 mesh on, among them, was measured to give 0.55 g/ml.

| Particle size distribution | 20 mesh on: | 0% by weight |
|---|---|---|
| | 20 mesh pass, 42 mesh on: | 3% by weight |
| | 42 mesh pass, 60 mesh on: | 10% by weight |
| | 60 mesh pass: | 87% by weight |

EXAMPLE 3

1900 Grams of the same sorbic acid as in Example 1, 2 g (0.024 mol) of sodium acetate and 4000 g of an aqueous solution of ethanol having a concentration of 60% by weight were fed to the same stirring vessel as in Example 1, and dissolved together by elevating the temperature up to 68° C., and thereafter cooled down to 30° C. over 6.5 hours with stirring at a revolution number of 150 rpm (by which the solution rotated comparatively slowly and the amount of air involved therein was small), to crystallize sorbic acid.

After separating the mother liquor by filtration, water-washing and drying were carried out in a conventional manner. The resulting crystals of sorbic acid (yield: 1480 g) had a hardness which was slightly lower than those obtained in Example 1 or Example 2 but sufficient for practical use.

The particle size distribution was as follows, and the bulk density of a portion having a particle size of 20 mesh pass and 42 mesh on, among them, was measured to give 0.61 g/ml.

| Particle size distribution | 20 mesh on: | 0% by weight |
|---|---|---|
| | 20 mesh pass, 42 mesh on: | 94% by weight |
| | 42 mesh pass, 60 mesh on: | 3% by weight |
| | 60 mesh pass: | 3% by weight |

COMPARATIVE EXAMPLE 3

Recrystallization was carried out in the same manner as in Example 3 except that no sodium acetate was added, to obtain crystals of sorbic acid which were much inferior both in the hardness and fluidity (yield: 1490 g).

The particle size distribution was as follows, and the bulk density of a portion having a particle size of 20 mesh pass and 42 mesh on, among them, was 0.39 g/ml.

| Particle size distribution | 20 mesh on: | 0% by weight |
|---|---|---|
| | 20 mesh pass, 42 mesh on: | 90% by weight |
| | 40 mesh pass, 60 mesh on: | 4% by weight |
| | 60 mesh on: | 6% by weight |

REFERENTIAL EXAMPLE a. 160 Grams of the same sorbic acid as in Example 1, and 6000 g of purified water were fed to the stirring vessel employed in Example 1, and dissolved by heating up to 98° C., and then cooled down to 30° C. over 12 hours with stirring at a revolution number of 150 rpm (the state inside the vessel was almost the same as in Example 3).

After separating the mother liquor by filtration, water-washing and drying were carried out. The resulting crystals of sorbic acid (yield: 138 g) were good in the particle size as mentioned below, but easily crushed. The bulk density of a portion having a particle size of 20 mesh pass and 42 mesh on was 0.41 g/ml.

| Particle size distribution | 20 mesh on: | 26% by weight |
|---|---|---|
| | 20 mesh pass, 42 mesh on: | 58% by weight |
| | 42 mesh pass, 60 mesh on: | 8% by weight |
| | 60 mesh pass: | 8% by weight | b. Recrystallization was carried out under the same conditions as the above-mentioned except that 6 g (0.1 mol) of sodium chloride was added. The resulting crystals of sorbic acid (yield: 136 g) were not improved at all as compared with the above-mentioned case a, and almost unchanged in the particle size (as mentioned below), fluidity and hardness, from those in the case a. The bulk density of a portion having a particle size of 20 mesh pass and 42 mesh on was 0.40 g/ml.

| Particle size distribution | 20 mesh on: | 27% by weight |
|---|---|---|
| | 20 mesh pass, 42 mesh on: | 60% by weight |
| | 42 mesh pass, 60 mesh on: | 7% by weight |
| | 60 mesh pass: | 6% by weight |

MEASUREMENT EXAMPLE

With the respective portions of the products (recrystallized sorbic acid) obtained in the above-mentioned Examples, Comparative examples and Referential example, the percentage powdering was measured in the manner mentioned below.

Fifty g was taken from the respective portions having a particle size of 20 mesh pass and 42 mesh on among the respective sorbic acid products obtained in the examples mentioned below. 0.1 Gram of an antistatic agent was added to the sample, and the resulting mixture together with 10 glass beads having a diameter of about 8 mm were fed to a sieve of 60 mesh, and shaken for 30 minutes with a low tap type sieve-shaker (made by Kabushiki Kaisha Isuzu Seisakusho, Japan), and the weight of fine powders having passed through the 60 mesh was weighed to obtain the percentage by weight based on the amount fed.

The results are shown below.

| | Percentage powdered |
|---|---|
| Example 1 | 0.3 |
| Example 2 | 0.7 |
| Example 3 | 1.9 |
| Comparative example 3 | 10 |
| Referential example (NaCl, not added) | 22 |
| Referential example (NaCl, added) | 20 |

As apparent from the above table, the powders of Comparative example 3 are easily powdered as compared with those of Example 3, and those of Referential example are much more easily crushed as compared with those of Examples.

What is claimed is:

1. In the method for producing crystals of sorbic acid by recrystallization with an aqueous solution of a lower aliphatic monovalent alcohol, the improvement which comprises employing 0.001 to 0.1 mol of an alkali metal ion as a crystal-modifying ion based on 1000 g of said aqueous solution of a lower aliphatic monovalent alcohol.

2. The method according to claim 1 wherein said alkali metal ion is sodium ion or potassium ion.

3. The method according to claim 1 wherein said alkali metal ion is produced from a compound selected from the group consisting of alkali metal hydroxides, alkali metal salts of halogenic acids, carbonic acid, sulfuric acid, boric acid, phosphoric acid and phosphorous acid, and alkali metal salts of aliphatic monocarboxylic acids, aliphatic polycarboxylic acids, aromatic carboxylic acids and aliphatic oxycarboxylic acids.

4. The method according to claim 1, or claim 2, or claim 3, wherein the temperature of said aqueous solution of an alcohol at which sorbic acid is dissolved therein is within the range of 20° C. to 70° C.

* * * * *